(12) United States Patent
Carlsen, Jr. et al.

(10) Patent No.: US 9,360,445 B2
(45) Date of Patent: Jun. 7, 2016

(54) RELATIVE HUMIDITY AND CONDENSATION MEASUREMENT WITH A CAPACITIVE HUMIDITY SENSOR

(75) Inventors: William F Carlsen, Jr., Coarsegold, CA (US); Hewlett E Melton, Jr., Sunnyvale, CA (US)

(73) Assignee: Carlsen Melton, Inc., Sunnyvale, CA (US)

( * ) Notice: Subject to any disclaimer, the term of this patent is extended or adjusted under 35 U.S.C. 154(b) by 810 days.

(21) Appl. No.: 13/374,343

(22) Filed: Dec. 21, 2011

(65) Prior Publication Data

US 2013/0166224 A1    Jun. 27, 2013

(51) Int. Cl.
*G01R 27/26* (2006.01)
*G06F 19/00* (2011.01)
*G01N 27/12* (2006.01)

(52) U.S. Cl.
CPC ................................. *G01N 27/121* (2013.01)

(58) Field of Classification Search
USPC .................... 324/663–690; 702/24
See application file for complete search history.

(56) References Cited

U.S. PATENT DOCUMENTS

| 4,295,090 A | 10/1981 | Ponkala |
| 4,295,091 A | 10/1981 | Ponkala |
| 4,636,714 A | 1/1987 | Allen |
| 6,647,782 B2 | 11/2003 | Toyoda |
| 6,888,358 B2 | 5/2005 | Lechner et al. |
| 7,032,448 B2 | 4/2006 | Hamamoto |

OTHER PUBLICATIONS

C Kolle and P O'Leary, "low-cost, high-precision measurement system for capacitive sensors" Measurement Science Technology, 1998, 510-517, vol. 9, IOP Publishing Ltd. UK.

*Primary Examiner* — Vincent Q Nguyen

(57) ABSTRACT

A method and apparatus for measuring relative humidity including condensing environmental conditions using a circuit with a capacitive humidity sensor and a reference resistor each connected to an input of a switch device and thence a quadrature sampling circuit. A sinusoidal source is first connected to the reference resistor and secondly to the capacitive humidity while a signal ground is first connected to the capacitive humidity sensor and secondly to the reference resistor. This produces a first voltage and a second voltage that are each sampled in quadrature. A complex ratio of the sampled voltages is calculated and converted into a representation of relative humidity.

15 Claims, 2 Drawing Sheets

RELATIVE HUMIDITY AND CONDENSATION MEASUREMENT WITH A CAPACITIVE HUMIDITY SENSOR

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

Prior Art

Capacitive humidity sensors are widely used for the determination of relative humidity as their capacitance changes nearly linearly with changes in relative humidity, they exhibit small hysteresis, have low temperature coefficients, and are highly reliable. Capacitive humidity sensors such as the JLC International HC103/HC104, GE Panametrics MiniCap-2, Rotronic CS 30, and Humirel 2030 are excellent examples of capacitive humidity sensors that are readily available in the market at the present time. Typically, the capacitances of these sensors range from 140 pF (picofarads) to 380 pF. Typical sensitivities (slope of capacitance versus relative humidity) range from 0.3 pF per % RH (percent relative humidity) to 0.5 pF per % RH. The temperature coefficients of these sensors are generally small, with values of up to 0.01 pF change per degree Celsius.

Capacitive humidity sensors generally require electronic circuitry, components, and devices to translate their capacitances to a convenient, readable, or usable form. Such electronic circuitry, components, and devices translate sensor capacitance to voltages, currents, frequency, and/or time. By means well known in the art, said voltages, currents, frequency, or time are then usually converted to a more convenient human readable form such as digital data or a number on a display which is representative of a relative humidity measured by the sensor. Within the scope of the present invention, "measurement circuit" and "measurement circuitry" shall be used to represent the electronic circuitry, components, and devices which provide a means for the measurement of voltages, currents, frequency, or time, and conversion of said voltages, currents, frequency, or time to a more convenient human readable form such as digital data or a number on a display. In addition, the terms "humidity sensor" and "humidity sensors" shall be used to represent one or a plurality of capacitive type humidity sensors.

Some applications of humidity sensors require accuracy approaching 0.1% RH. Resolving 0.1% RH with a typical humidity sensor, requires measuring its capacitance to an accuracy of 30 fF (femtofarads) to 50 fF, or approximately 1 part in 10,000. At this level of performance, not only must measurement circuitry be capable of an accuracy of 1 part in 10,000 in capacitance, but parasitic capacitance and parasitic conductance arising from a sensor's measurement circuitry needs to be known and stable to 1 part in 10,000 or better. In addition, this level of performance must be maintained over the full range of operating temperatures and relative humidity's encountered.

A practical alternating current circuit model for a humidity sensor, operated at a frequency f, consists of two components: an ideal capacitor, with capacitance $C_x$ and susceptance $B_x = 2\pi f C_x$, connected in parallel with a frequency dependent resistance $R_x$ and its conductance $G_x = 1/R_x$. The parallel conductance $G_x$ accounts for both the capacitive dielectric loss and the current leakage of the humidity sensor. In complex notation, the admittance $Y_x$ for the humidity sensor is:

$$Y_x = G_x + jB_x$$

The measurement circuitry of a humidity sensor may add a parasitic admittance. This parasitic admittance $Y_p$, consists of a parasitic susceptance $B_p$ and a parasitic conductance $G_p$ both of which act in parallel with the humidity sensor. In complex notation, the parasitic admittance $Y_p$ is:

$$Y_p = G_p + jB_p$$

The parasitic susceptance $B_p$ adds to the humidity sensor's apparent susceptance for a total susceptance of $B_x + B_p$. The parasitic conductance $G_p$ adds to the humidity sensor's apparent conductance for a total conductance of $G_x + G_p$. Parasitic susceptance and parasitic conductance can thereby lead to measurement errors in determining relative humidity. Not only does parasitic admittance create a fixed error in measurement of relative humidity, but it often varies undesirably and unpredictably with changes in environmental conditions both during manufacturing and during use, making the accurate determination of relative humidity difficult.

Environmental conditions can often affect the operation of measurement circuitry causing changes in: device admittances, parasitic admittances, frequencies, currents, offset currents, leakage currents, voltages, threshold voltages, offset voltages, component values, temperature coefficients and overall measurement circuit gains. These environmental conditions can include dust, chemical vapor(s), water vapor, water condensation, air currents, and temperature, or combinations thereof. For example, under condensing environmental conditions, liquid water on surfaces of a humidity sensor and its measurement circuitry can mix with surface dust and other surface compounds. This then can lead to a large increase in total conductance and susceptance, thereby causing large measurement errors, and even stopping measurement circuit operation altogether. Such undesirable and unpredictable changes present demanding measurement challenges that are not taught in the prior art.

Early exemplary prior art is found in U.S. Pat. Nos. 4,295,090 and 4,295,091 wherein is taught the use of an integrator comprising a humidity sensor as an ideal capacitance connected as a feedback element between an amplifier's input and output, and a resistor connected to the amplifier's input. With the humidity sensor as the feedback capacitance, the amplifier is less sensitive to parasitic capacitances at its input and output. In operation, the integrator repeatedly charges and discharges the humidity sensor. The output of the integrator connects to an input of a comparator having a threshold voltage. When the output of the integrator alternately crosses the threshold voltage of the comparator, the comparator alternately changes its output between high and low voltage. The output of the comparator is then fed back to drive the integrator charge and discharge cycles. The frequency of the signal at the output of the comparator is thereby dependent on the capacitance of the humidity sensor. U.S. Pat. Nos. 4,295,090 and 4,295,091, however, do not account for changes in comparator threshold voltage, offset voltages, offset currents, or for changes in high and low output voltages of the comparator. Changes in these parameters can cause undesired changes in the charge and discharge of the capacitive humidity sensor, undesired changes in the oscillation frequency, and thereby erroneous indications of changes in relative humidity. In addition, under condensing conditions, values of capacitance and conductance for a humidity sensor can increase by orders of magnitude, causing failure of the charge or discharge of the integrator to reach threshold voltage, halting oscillation.

Additional exemplary prior art is found in U.S. Pat. Nos. 4,636,714, and 6,647,782, and 6,888,358, and 7,032,448 wherein humidity sensors are taught as ideal capacitors incorporated into a switched capacitor circuit. The circuits comprise an amplifier with a reference capacitor $C_R$ and a parallel connected switch as feedback elements. Not taught or anticipated by these patents are offset voltage errors that arise from operation of the feedback switch, which exhibits different offsets between its closed and open states. When the feedback switch is closed a voltage appears at the amplifier's output equal to its input offset voltage, $V_{osclosed}$. When the feedback switch is open, another offset voltage $V_{osopen}$ arises due to the feedback capacitor $C_R$ and due to all capacitances connected to the inverting input of the amplifier. These include a capacitive humidity sensor with capacitance $C_x$ and conductance $G_x$, other parasitic capacitances $C_p$, and parasitic conductances $G_p$. $V_{osopen}$ is given by:

$$V_{osopen} = V_{osclosed} + V_{osclosed}\left(\frac{C_x + C_p}{C_R} + \frac{G_x + G_p}{C_R}t\right).$$

An elapsed time t is determined upon opening of the feedback switch. In addition, an input bias current $I_b$ to the amplifier causes an additional offset voltage $V_{osIb}$ that can be approximated as follows:

$$V_{osIb} \approx \frac{I_b t}{C_R}.$$

In U.S. Pat. Nos. 6,647,782 and 7,032,448, no offset correction is taught or anticipated for $V_{osclosed}$ or for $V_{osopen}$. In U.S. Pat. Nos. 4,636,714, and 6,647,782, 6,888,358, and 7,032,448 an offset correction is taught for $V_{osclosed}$ without anticipation of additional offset errors, namely:

$$V_{osclosed}\left(\frac{C_x + C_p}{C_R} + \frac{G_x + G_p}{C_R}t\right) + \frac{I_b t}{C_R}$$

In addition, none of these patents anticipate condensing conditions, where values of humidity sensor capacitance and conductance increase by orders of magnitude, thereby causing offset changes during switching that can lead to erroneous, even meaningless humidity indications.

Additional exemplary prior art is found in a paper published in Measurement Science Technology, Vol. 9, 1998, pages 510-517, by Kolle and O'Leary entitled "Low-cost, high-precision measurement system for capacitive sensors". Kolle and O'Leary teach a circuit and method for measuring humidity using a humidity sensor and a current-to-voltage converter with a reference resistor, whereby the humidity sensor's capacitance and its conductance are measured using quadrature detection methods. These measurements are less sensitive to variations in offsets, parasitic admittance, reference signal source amplitude, and circuit gain.

In particular, Kolle and O'Leary teach a two part quadrature modulation to obtain two quadrature signals whereby one quadrature signal is subtracted from the other to remove offset voltage. In addition, the signal input of a current-to-voltage converter is periodically switched between a reference resistor and a humidity sensor as a means for an auto-calibration. A ratio is calculated between the response when the humidity sensor is connected and the response when the reference resistor is connected. This ratio ideally cancels out circuit gain and its variations, and signal source amplitude and its variations from the determination of humidity sensor capacitance. However, Kolle and O'Leary do not account for the loop gain difference between when the humidity sensor or when the reference resistor is connected to the input of the current-to-voltage converter. Loop gain, well known in the prior art of feedback control, includes a feedback factor β which depends on the ratio of feedback admittance to the sum of feedback admittance and current-to-voltage converter input admittance.

With the humidity sensor connected, the total input admittance is the sum of the admittance of the humidity sensor $Y_x$, the parasitic admittance of the circuit $Y_p$, the admittance of the current-to-voltage converter input $Y_a$, and the total feedback admittance $Y_f$. In this case, the feedback factor is given by:

$$\beta_{sensor\ connected} = \frac{Y_f}{Y_x + Y_p + Y_a + Y_f}$$

On the other hand, with the reference resistor connected, the total input admittance is the sum of the reference resistor's conductance $G_r$, the parasitic admittance of the circuit $Y_p$, the admittance of the current-to-voltage converter input $Y_a$, and the total feedback admittance $Y_f$. In this case, the feedback factor is given by:

$$\beta_{ref\ resistor\ connected} = \frac{Y_f}{G_r + Y_p + Y_a + Y_f}$$

As the loop gain of the circuit depends on the feedback factor β, the loop gain differs depending on whether the humidity sensor or the reference resistor is connected to the current-to-voltage converter. The ratio computed by Kolle et al, therefore, does not lead to complete correction for a) the parasitic admittance of the circuit, b) the reference signal source amplitude, c) the overall circuit gain, or d) for their variations. In addition, under condensing environmental conditions, the conductance of the humidity sensor can increase dramatically, causing the gain of the current-to-voltage converter coupled to the humidity sensor to increase by many orders of magnitude. This results in distortion or severe limiting of the current-to-voltage converter's output signal, or in unwanted oscillation of the current-to-voltage converter, thereby leading to grossly erroneous indications of relative humidity.

SUMMARY

An objective of the present invention is to overcome the disadvantages of prior art to assure accurate measurement of relative humidity when using a capacitive humidity sensor.

A second objective of the present invention is to overcome the disadvantages of prior art to assure continued, sensible and reproducible indications under condensing conditions when using a capacitive humidity sensor.

A third objective of the present invention is to overcome the disadvantages of prior art to assure sensible and continuous indications during the transition from non-condensing to condensing conditions when using a capacitive humidity sensor.

These objectives are advantageously attained by an embodiment comprising:

a) A quadrature sampling circuit having it's input connected to an output of a humidity sensor and an output of a reference resistor.

Quadrature sampling circuits are well known in the prior art for determining the real and imaginary components of a sinusoidal signal. In the context of an embodiment of the present invention, a quadrature sampling circuit is a circuit that samples a sinusoidal signal synchronously with said signal. Sample times within a given period of the sinusoidal signal occur at $$t_{sample} = m\left(\frac{T}{4}\right)$$

where T=the period of the sinusoidal signal
m=0, 1, 2, 3 representing four samples taken in a given period b) An input of the humidity sensor and an input of the reference resistor are alternately connected to a signal ground or a sinusoidal source by a double-pole double-throw (DPDT) switch having two switch states. The two states of the DPDT switch result in a first voltage and a second voltage.)

c) The first voltage is generated when the DPDT switch is configured to connect the input of the humidity sensor to signal ground and the input of the reference resistor to the sinusoidal source.

d) The second voltage is generated when the DPDT switch is configured to connect the input of the humidity sensor to the sinusoidal source and the input of the reference resistor to signal ground.

e) The first and second voltages are both sinusoidal. The quadrature sampling circuit creates a first and second set of data samples from the first and second voltages, respectively.

f) A computer determines a first peak-to-peak complex voltage from the first set of data samples, and determines a second peak-to-peak complex voltage from the second set of data samples.

In the context of an embodiment of the present invention, the peak-to-peak complex voltage is derived from the difference of real components separated by T/2 and the difference of imaginary components separated by T/2.

g) The computer then takes a complex ratio of the second complex peak-to-peak voltage to the first complex peak-to-peak voltage. Said complex ratio cancels out parasitic admittance, voltage offsets, the sinusoidal source amplitude, and measurement circuitry gain.

h) From the complex ratio, the computer calculates a value representative of relative humidity.

Some unique advantages of using the previously described embodiment include:

a) elimination of gain changes due to switch operation by using a voltage follower that has a gain unaffected by switch operation;

b) elimination of off-set errors by the measurement of peak-to-peak complex voltages;

c) elimination of undesired parasitic admittance by using the complex ratio of peak-to-peak complex voltages;

d) elimination of undesired variations in sinusoidal source amplitude by using a complex ratio of peak-to-peak complex voltages;

e) elimination of variations in measurement circuit gain by using a complex ratio of peak-to-peak complex voltages; and f) elimination of distortion or severe limiting during condensing conditions by providing for peak-to-peak complex voltages that are equal to or smaller than the sinusoidal source even when humidity sensor admittance increases by many orders of magnitude thereby assuring continued, sensible and reproducible indications under condensing conditions and during the transition between non-condensing and condensing conditions.

DRAWINGS

DETAILED DESCRIPTION

Figure 1:
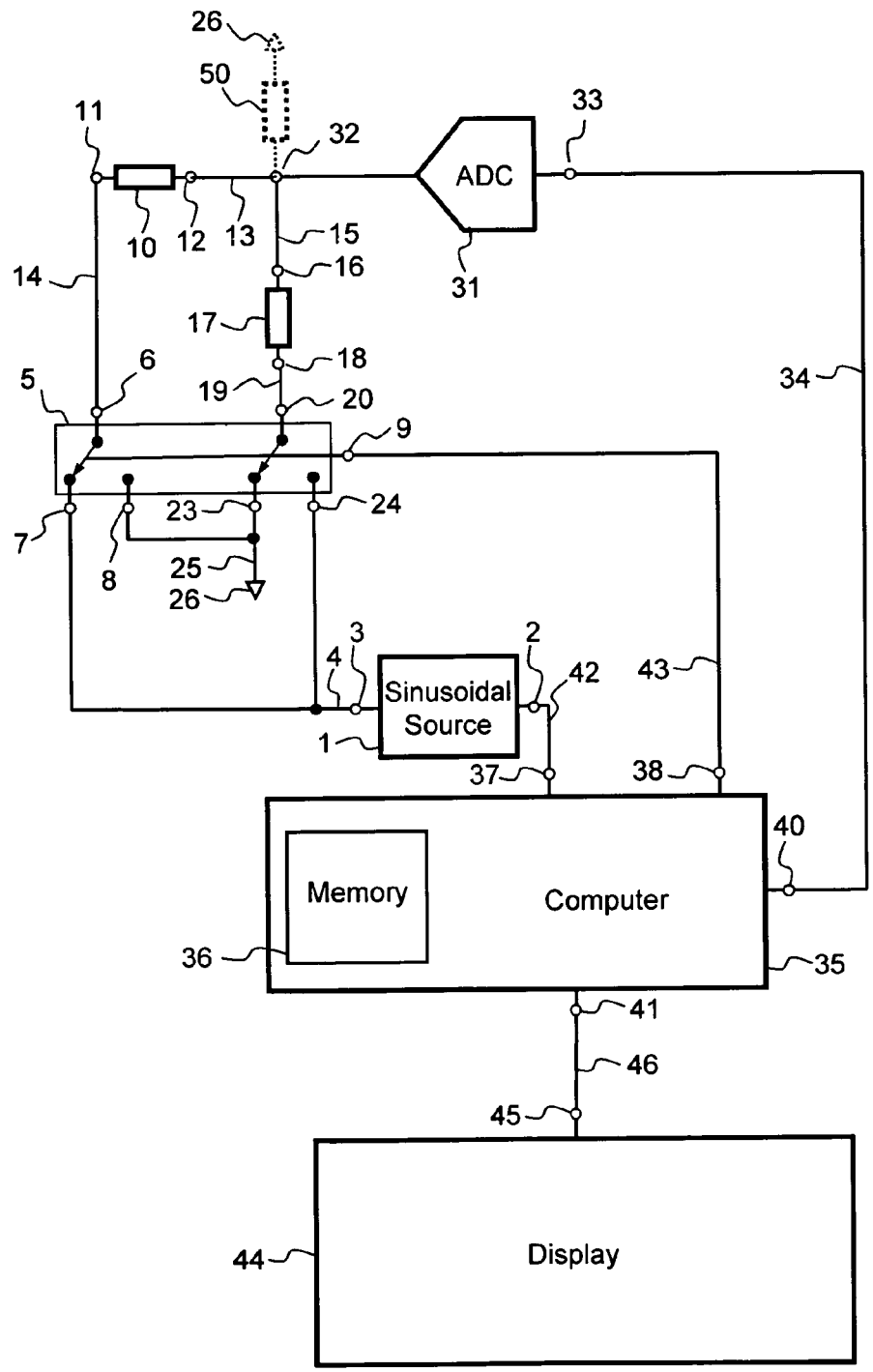
FIG. 1 shows an embodiment for accurate measurement of relative humidity using a capacitive humidity sensor.

Shown in FIG. 1 is an embodiment for accurate measurement of relative humidity comprising the following components: a humidity sensor 17, a reference resistor 10, an electronically actuated double-pole double-throw (DPDT) switch 5, a sinusoidal source 1 capable of producing a sinusoidal signal, an analog-to-digital converter (ADC) 31, a computer 35 containing a memory 36, and a display 44. Memory 36 contains a set of instructions for execution by computer 35 that include controlling sinusoidal source 1, controlling DPDT switch 5, controlling ADCC 31, controlling display 44, and for performing mathematical calculations. In addition, memory 36 contains a set of calibration data which relate a plurality of complex ratios to a corresponding plurality of values of relative humidity. Also illustrated is a parasitic admittance 50.

DPDT switch 5 includes a first input 7, a second input 8, and a first output 6. First output 6 is connected either to first input 7 or second input 8 dependent on a control input 9. DPDT switch 5 also includes a third input 23, a fourth input 24, and a second output 20. Second output 20 is connected either to third input 23 or fourth input 24 dependent on control input 9.

Sinusoidal source 1 includes a digital port 2 and an output 3. Reference resistor 10 includes an input 11 and an output 12. Humidity sensor 17 includes an input 18 and output 16. ADC 31 includes an input 32 and a digital port 33. Computer 35 includes a first digital port 37, a second digital port 38, a third digital port 40, and a fourth digital port 41. Display 44 includes a digital port 45.

Digital port 2 of sinusoidal source 1 is connected to first digital port 37 of computer 35 via a connection 42. Output 3 of sinusoidal source 1 is connected to first input 7 and to fourth input 24 of DPDT switch 5 via a connection 4. A signal ground 26 is connected to second input 8 and to third input 23 of DPDT switch 5 via a connection 25. First output 6 of DPDT switch 5 is connected to input 11 of reference resistor 10 via a connection 14. Second output 20 of DPDT switch 5 is connected to input 18 of humidity sensor 17 via a connection 19. Output 12 of reference resistor 10 and output 16 of humidity sensor 17 are both connected to input 32 of ADC 31 via a connection 13 and a connection 15 respectively. Control input 9 of DPDT switch 5 is connected to second digital port 38 of computer 35 via a connection 43. Parasitic admittance 50 is connected between input 32 of ADC 31 and signal ground 26.

Third digital port 40 of computer 35 is connected to digital port 33 of ADC 31 via a connection 34. Fourth digital port 41 of computer 35 is connected to digital port 45 of display 44 via a connection 46.

Figure 2A:
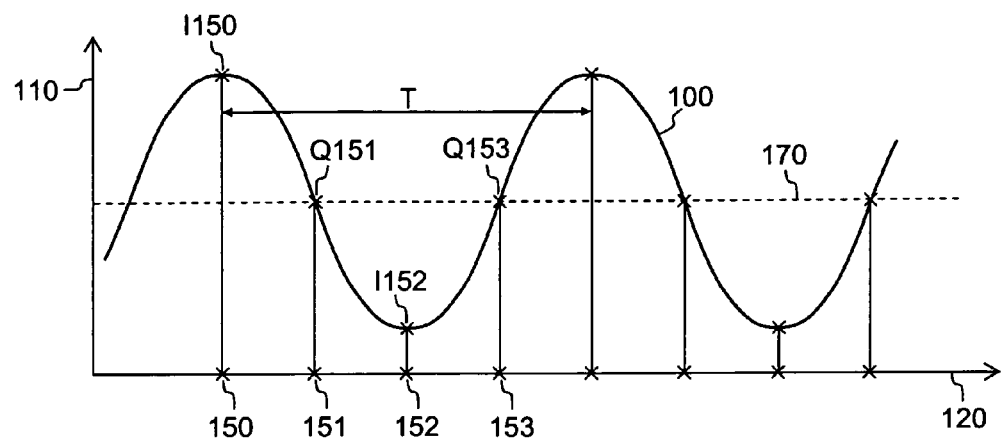
FIG. 2A illustrates the timing for quadrature sampling of a first voltage.

A measurement responsive to relative humidity is performed as follows:

A first operation executed by computer 35 includes:
- a) Computer 35, via connection 43, actuates DPDT switch 5, connecting first output 6 to first input 7 of DPDT switch 5, and connecting second output 20 to third input 23 of DPDT switch 5. This, thereby, connects output 3 of sinusoidal source 1 to input 11 of reference resistor 10 and connects input 18 of humidity sensor 17 to signal ground 26. This, thereby, produces a first voltage at input 32 of ADC 31.
- b) Computer 35, via connection 34, then causes ADC 31 to quadrature sample and convert the first voltage synchronously with sinusoidal source 1, creating a first set of data samples. FIG. 2A is an illustration of the timing for quadrature sampling the first voltage. A first voltage 100 is substantially sinusoidal with a horizontal time axis 120 and a vertical voltage axis 110. First voltage 100 has substantially the same frequency as sinusoidal source 1 (whereas their relative phase and amplitude may be different). The frequency f of first voltage 100 determines a time period T where:

$$T = \frac{1}{f}.$$

Sample times for ADC 31 are denoted sequentially by 150, 151, 152 and 153. Sample time 150 occurs at a fixed time with respect to sinusoidal source 1. Subsequent sample times 151, 152 and 153 are spaced by one-fourth of period T. At these sample times, first voltage 100 has voltage values I150, Q151, I152, and Q153 corresponding to sample times 150, 151, 152, and 153 respectively.
- c) Computer 35 then causes ADC 31 to transfer the first set of data samples to computer 35. Computer 35 then stores the first set of data samples in memory 36.
- d) With the first set of data samples, Computer 35 then subtracts the voltage value taken at sample time 152 from the voltage value taken at sample time 150, giving a peak-to-peak real component $I_1$ of the first voltage where:

$I_1 = I150 - I152$

Computer 35 also subtracts the voltage value taken at sample time 153 from the voltage value taken at sample time 151, giving a peak-to-peak imaginary component $Q_1$ of the first voltage where:

$Q_1 = Q151 - Q153$

A first complex peak-to-peak voltage, comprising the peak-to-peak real and peak-to-peak imaginary components of the first voltage, is then stored in memory 36 as a first result $R_1$ where:

$R_1 = I_1 + jQ_1$

Figure 2B:
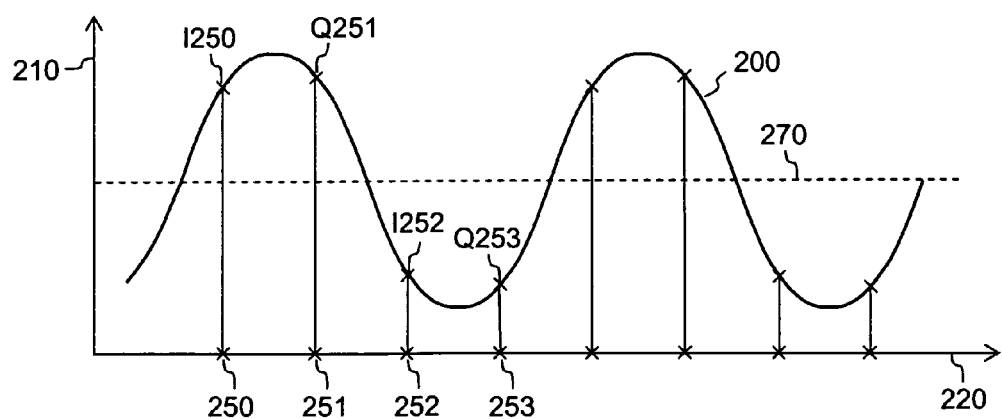
FIG. 2B illustrates the timing for quadrature sampling of a second voltage.

A second operation executed by computer 35 includes
- a) Computer 35, via connection 43, actuates DPDT switch 5, connecting first output 6 to second input 8 of DPDT switch 5, and connecting second output 20 to fourth input 24 of DPDT switch 5. This, thereby, connects output 3 of sinusoidal source 1 to input 18 of humidity sensor 17 and input 11 of reference resistor 10 to signal ground 26. This, thereby, produces a second voltage at input 32 of ADC 31.
- b) Computer 35, via connection 34, then causes ADC 31 to quadrature sample and convert the second voltage synchronous with sinusoidal source 1, creating a second set of data samples. FIG. 2B is an illustration of the timing for quadrature sampling the second voltage. A second voltage 200 is substantially sinusoidal with a horizontal time axis 220 and a vertical voltage axis 210. Second voltage 200 has substantially the same frequency as sinusoidal source 1 (whereas their relative phase and amplitude may be different). The frequency f of second voltage 200 determines a time period T where:

$$T = \frac{1}{f}$$

Sample times for ADC 31 are denoted sequentially by 250, 251, 252 and 253. Sample time 250 occurs at a fixed time with respect to the sinusoidal source 1. Subsequent sample times 251, 252 and 253 are spaced by one-fourth of period T. At these sample times, second voltage 200 has voltage values I250, Q251, I252, and Q253 corresponding to sample times 250, 251, 252, and 253 respectively.
- c) Computer 35 then causes ADC 31 to transfer the second set of data samples to computer 35. Computer 35 then stores the second set of data samples in memory 36.
- d) With the second set of data samples, computer 35 then subtracts the voltage value taken at sample time 252 from the voltage value taken at sample time 250, giving a peak-to-peak real component $I_2$ of the second voltage where:

$I_2 = I250 - I252$

Computer 35 also subtracts the voltage value taken at sample time 253 from the voltage value taken at sample time 251, giving a peak-to-peak imaginary component $Q_2$ of the second voltage where:

$Q_2 = Q251 - Q253$

A second complex peak-to-peak voltage comprising the peak-to-peak real and peak-to-peak imaginary component of the second voltage, is then stored in memory 36 as a second result $R_2$ where:

$R_2 = I_2 + jQ_2$

An electronic circuit analysis of the embodiment illustrated in FIG. 1, gives the following values for $R_1$ and $R_2$:

$$R_1 = KV_s \frac{G_r}{G_r + Y_x + Y_p}$$

$$R_2 = KV_s \frac{Y_x}{G_r + Y_x + Y_p}$$

where K is an overall circuit gain, $V_s$ is a peak-to-peak amplitude voltage of sinusoidal source 1 at output 3, $G_r$ is the conductance value of reference resistor 10, $Y_x$ is the admittance value of humidity sensor 17, and $Y_p$ is the admittance value of parasitic admittance 50.

Computer 35 then computes $R_2$ divided by $R_1$ as a complex ratio $R_3$ as a third result, and stores the third result in memory 36. The third result $R_3$ can be written as follows:

$$R_3 = \frac{R_2}{R_1} = \frac{I_2 + jQ_2}{I_1 + jQ_1} = \left(\frac{I_1 I_2 + Q_1 Q_2}{I_1^2 + Q_1^2}\right) + j\left(\frac{Q_2 I_1 - Q_1 I_2}{I_1^2 + Q_1^2}\right) = I_3 + jQ_3.$$

Substituting in the electronic circuit analysis values from above gives:

$$R_3 = \frac{KV_s \dfrac{Y_x}{G_r + Y_x + Y_p}}{KV_s \dfrac{Y_x}{G_r + Y_x + Y_p}} = \frac{Y_x}{G_r} = \frac{G_x}{G_r} + j\frac{B_x}{G_r} = \frac{G_x}{G_r} + j\frac{\omega C_x}{G_r}.$$

The third result $R_3$, as shown above, consists of components $I_3$ and $Q_3$. Component $I_3$ is directly proportional to sensor conductance $G_x$. Component $Q_3$ is directly proportional to sensor susceptance $B_x$, whereby the relative humidity seen by humidity sensor 17 is a function of sensor susceptance $B_x$.

Computer 35 then converts the susceptance $B_x$ into a display value of relative humidity and sends the display value to display 44 via connection 46 for viewing.

Alternative Embodiments

Alternatively $R_3$ could be a ratio of $R_1$ to $R_2$. This then results in an equivalent series impedance $Z_{sx}$ for humidity sensor 17 consisting of a series resistance $R_{sx}$ and series reactance $X_{sx}$ written as:

$$Z_{sx} = R_{sx} - jX_{sx} = R_{sx} - j\frac{1}{\omega C_{sx}}$$

A value of relative humidity may then be derived from $X_{sx}$.

Alternatively, more than 1 set of 4 data samples per period may be taken allowing for computing a plurality of peak-to-peak real and imaginary components for the first set of data samples and a plurality of peak-to-peak real and imaginary components for the second set of data samples. This then gives a plurality of complex ratios and a corresponding plurality of display values of relative humidity. This would allow for the display of relative humidity values as a function of time.

This would also allow an averaging of relative humidity values over time to provide an improvement in signal to noise ratio. Furthermore, a plurality of peak-to-peak real and peak-to-peak imaginary samples for the first complex peak-to-peak voltage could be averaged, and a plurality of peak-to-peak real and imaginary samples for the second complex peak-to-peak voltage could be averaged to improve signal-to-noise of the complex ratio. This could thereby the improve the signal-to-noise ration of the indicated relative humidity.

Alternatively, quadrature samples, as shown in the above embodiment, need not occur all in one period of the sinusoidal source. They may also be spaced by integral multiples of the voltage period T such that the time between samples is then $$t_{sample} = nT + m\left(\frac{T}{4}\right)$$

where n is an integer, and m=0,1,2,3 for each of the four quadrature samples of the first and second voltages.

Alternatively, DPDT Switch 5 could be replaced by any plurality of switches wired in such a way as to be substantially equivalent to the function of the DPDT switch described herein.

Alternatively, sinusoidal source 1 could comprise a digital to analog converter, having an output 3, that converts digital data fed to an input 2 from computer 35, or could comprise an analog oscillator, having an output 3, synchronized with computer 35 via an input 2, or could comprise a direct digital synthesis circuit with an output 3 that is controlled by data fed to an input 2 from computer 35.

Alternatively, a voltage follower having a gain one or less with an input connected to output 12 of reference resistor 10 and output 16 of capacitive humidity sensor 17 and with an output connected to input 32 of ADC 31 could be placed in the circuit. This would ensure that input voltages to ADC 31 are limited regardless of the impedance of the humidity sensor, such as in condensing conditions.

In addition, integrated circuits could comprise a plurality of the components and connections of the embodiment of FIG. 1 without departing from the spirit and scope of the present invention.

Advantages

From the description above, a number of advantages of some of the embodiments of the present invention become evident:

a) The complex ratio used to compute third result $R_3$ cancels out the parasitic admittance $Y_p$, the overall circuit gain K, and the sinusoidal source amplitude $V_s$. Third result $R_3$ is thereby independent of parasitic admittance and its variation, independent of sinusoidal source amplitude and its variation, and independent of overall circuit gain and its variation.

b) The use of peak-to-peak complex values removes any DC offsets created by the switch or the ADC.

c) The electronic circuit arrangement removes loop gain differences and responds without fail for all values of the sensor admittance $Y_x$, thereby ensuring accurate measurement of relative humidity and continued, sensible and reproducible indications under condensing conditions.

d) Consequently, sensor susceptance $B_x$ (the imaginary part of third result $R_3$) and thereby measured relative humidity, is independent of undesired variations due to many environmental influences on measurement circuitry.

Conclusion, Ramifications, And Scope

Accordingly, the advantageous circuit arrangements and calculations described above overcome the disadvantages of prior art a) by eliminating undesirable off-set errors;
b) by eliminating undesirable differences in loop gain;
c) by canceling undesirable parasitic admittance;
d) by canceling undesirable gain dependence;
e) by eliminating undesirable humidity and temperature influences on circuitry, components and devices;
f) and by eliminating undesirable gross errors or failure of measurement circuitry in condensing conditions and in transitions between non-condensing and condensing conditions.

Various changes in the form and details of this invention by those skilled in the art may be made without departing from the spirit and scope of the present invention.

What is claimed is:

1. An electronic circuit arrangement for measuring relative humidity comprising:
   a. a quadrature sampling circuit having an input and an output;
   b. a capacitive humidity sensor having an input and an output wherein the output of the capacitive humidity sensor is connected to the input of the quadrature sampling circuit;
   c. a reference resistor, having an input and an output wherein the output of the reference resistor is connected to the input of the quadrature sampling circuit;
   d. a sinusoidal source having an output;
   e. a plurality of switches having a first state and a second state, wherein
      i. the first state comprises connecting the input of the capacitive humidity sensor to a signal ground and the input of the reference resistor to the output of the sinusoidal source, producing a first voltage at the input of the quadrature sampling circuit and
      ii. the second state comprises connecting the input of the capacitive humidity sensor to the output of the sinusoidal source and the input of the reference resistor to the signal ground, producing a second voltage at the input of the quadrature sampling circuit;
   f. a computer having in input wherein the output of the quadrature sampling circuit is connected to the input of the computer;
   g. wherein said quadrature sampling circuit digitizes a plurality of quadrature-samples of the first voltage producing a first set of data samples, and digitizes a plurality of quadrature-samples of the second voltage producing a second set of data samples;
   h. wherein said computer
      i. computes a first peak-to-peak complex voltage from the first set of data samples, and
      ii. computes a second peak-to-peak complex voltage from the second set of data samples, and
      iii. computes the complex ratio of the first peak-to-peak complex voltage and second peak-to-peak complex voltage, and
      iv. from said complex ratio, computes a value representative of relative humidity.

2. The electronic circuit arrangement of claim 1 further including a voltage follower having an input and an output wherein the input of the voltage follower is connected to the outputs of the reference resistor and the capacitive humidity sensor and the output of the voltage follower is connected to the input of the quadrature sampling circuit.

3. The electronic circuit arrangement of claim 2 wherein an integrated circuit comprises the computer, the sinusoidal source, the analog-to-digital converter, the plurality of switches, the reference resistor, the capacitive humidity sensor, and the voltage follower.

4. The electronic circuit arrangement of claim 1 wherein the plurality of switches is electronically actuated by the computer.

5. The electronic circuit arrangement of claim 3 wherein the plurality of switches comprises a double-pole double-throw switch.

6. The electronic circuit arrangement of claim 3 wherein the plurality of switches comprises two single-pole double-throw switches.

7. The electronic circuit arrangement of claim 1 wherein the sinusoidal source comprises a digital to analog converter.

8. The electronic circuit arrangement of claim 1 wherein an integrated circuit comprises the computer and the sinusoidal source.

9. The electronic circuit arrangement of claim 1 wherein an integrated circuit comprises the computer, the sinusoidal source, and the analog-to-digital converter.

10. The electronic circuit arrangement of claim 1 wherein an integrated circuit comprises the computer, the sinusoidal source, the analog-to-digital converter, and the plurality of switches.

11. The electronic circuit arrangement of claim 1 wherein an integrated circuit comprises the computer; the sinusoidal source, the analog-to-digital converter, the plurality of switches, and the reference resistor.

12. The electronic circuit arrangement of claim 1 wherein an integrated circuit comprises the computer, the sinusoidal source, the analog-to-digital converter, the plurality of switches, the reference resistor, and the capacitive humidity sensor.

13. A method for measuring relative humidity comprising:
   a. providing a quadrature sampling circuit having an input and an output wherein the output of the quadrature sampling circuit is connected to a computer;
   b. providing a capacitive humidity sensor having an input and an output wherein the output of the capacitive humidity sensor is connected to the input of the quadrature sampling circuit;
   c. providing a reference resistor, having an input and an output wherein the output of the reference resistor is connected to the input of the quadrature sampling circuit;
   d. providing a sinusoidal source having an output;
   e. providing a plurality of switches having a first state and a second state, wherein
      i. the first state connects the input of the capacitive humidity sensor to a signal ground and the input of the reference resistor to the output of the sinusoidal source, producing a first voltage at the input of the quadrature sampling circuit, and
      ii. the second state connects the input of the capacitive humidity sensor to the output of the sinusoidal source and the input of the reference resistor to the signal ground, producing a second voltage at the input of the quadrature sampling circuit;
   f. digitizing with said quadrature sampling circuit a plurality of quadrature-samples of the first voltage producing an output of a first set of data samples, and a plurality of quadrature-samples of the second voltage producing a second set of data samples;
   g. computing with said computer
      i. a first peak-to-peak complex voltage from the first set of data;
      ii. a second peak-to-peak complex voltage from the second set of data samples;
      iii. a complex ratio of the first and second peak-to-peak complex voltages;
      iv. a value representative of relative humidity from said complex ratio.

14. The method for measuring relative humidity of claim 13 further providing a voltage follower having an input and an output wherein said input of voltage follower is connected to the outputs of the reference resistor and the capacitive humidity sensor and the output of the voltage follower is connected to the input of the quadrature sampling circuit.

15. The method for measuring relative humidity of claim 13 wherein the plurality of switches is electronically actuated by the computer.

* * * * *